(12) United States Patent
Axelgaard

(10) Patent No.: US 8,473,072 B2
(45) Date of Patent: Jun. 25, 2013

(54) CUSTOMIZABLE MEDICAL ELECTRODE

(75) Inventor: Jens Axelgaard, Fallbrook, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 300 days.

(21) Appl. No.: 12/796,561

(22) Filed: Jun. 8, 2010

(65) Prior Publication Data

US 2011/0301683 A1  Dec. 8, 2011

(51) Int. Cl.
*A61N 1/00* (2006.01)
*A61B 5/04* (2006.01)

(52) U.S. Cl.
USPC .......................................... 607/115; 600/372

(58) Field of Classification Search
USPC ........... 607/115, 142, 148–149, 152; 600/372
See application file for complete search history.

(56) References Cited

U.S. PATENT DOCUMENTS

| | | | |
|---|---|---|---|
| 4,736,752 A | 4/1988 | Munck et al. | |
| 4,867,166 A | 9/1989 | Axelgaard et al. | |
| 5,085,217 A | 2/1992 | Shimizu | |
| 5,450,845 A | 9/1995 | Axelgaard | |
| 5,678,545 A | 10/1997 | Stratbucker | |
| 5,904,712 A | 5/1999 | Axelgaard | |
| 7,171,276 B2 | 1/2007 | Giuntoli et al. | |
| 7,206,630 B1 | 4/2007 | Tarler | |
| 7,324,847 B2 | 1/2008 | Axelgaard | |
| 7,715,921 B2* | 5/2010 | Palti .............................. | 607/115 |
| 8,352,045 B2* | 1/2013 | Joucla et al. .................. | 607/116 |
| 2005/0251241 A1 | 11/2005 | Axelgaard | |
| 2007/0169333 A1 | 7/2007 | Donoghue et al. | |
| 2007/0238944 A1* | 10/2007 | Axelgaard ..................... | 600/372 |
| 2008/0065182 A1* | 3/2008 | Strother et al. ............... | 607/115 |
| 2011/0071611 A1* | 3/2011 | Khuon et al. .................. | 607/142 |

* cited by examiner

Primary Examiner — Christopher D Koharski
Assistant Examiner — Catherine Voorhees
(74) Attorney, Agent, or Firm — Hackler Daghighian & Martino

(57) ABSTRACT

A medical electrode includes a conductive member having a top and a bottom side and a plurality of cutouts establishing a pattern of islands interconnected by conductive member bridges. A plurality of island electrodes are provided with each island electrode disposed on a corresponding island. A conductive adhesive is disposed on the conductive member bottom side for adhering the medical electrode to a patient's skin.

23 Claims, 4 Drawing Sheets

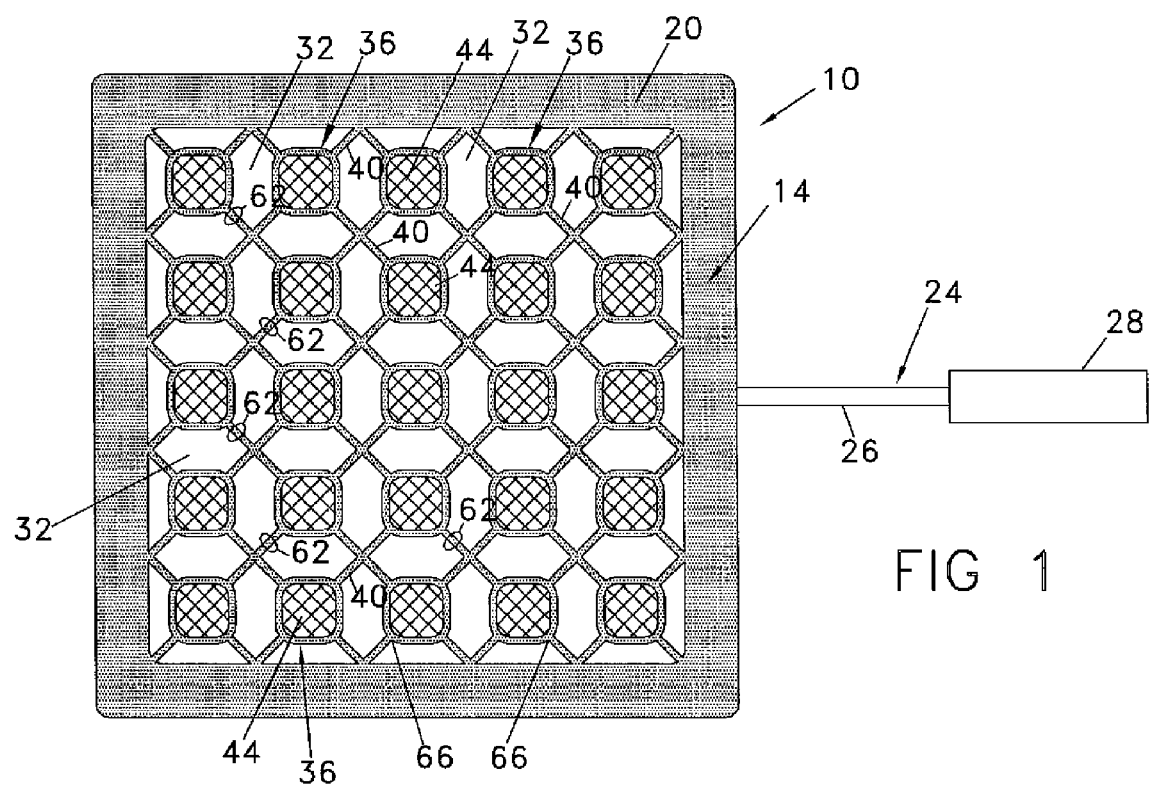
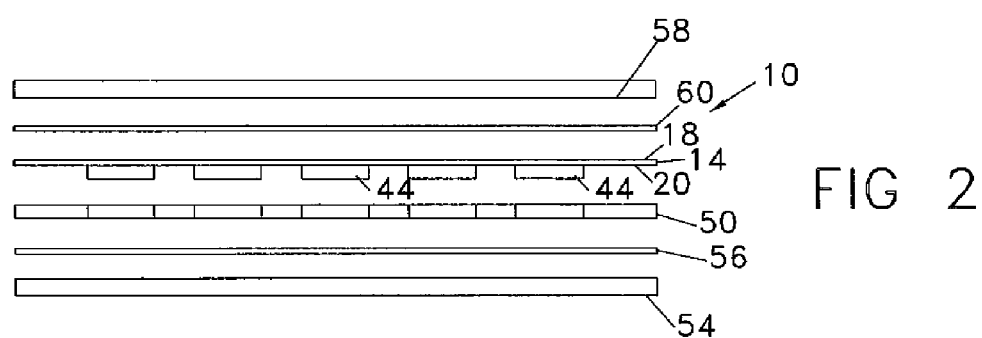

CUSTOMIZABLE MEDICAL ELECTRODE

The present invention generally relates to electrodes and, more particularly, electrodes suitable for transcutaneous nerve and/or muscle stimulation and biological signal recording.

With regard to transcutaneous nerve and/or muscle stimulation, medical electrodes must provide an even electrical distribution to a patient's skin over an entire surface of the electrode to effect proper coupling. Because of the curvaceous nature of the human body, it is apparent that medical electrodes for use thereon must be flexible not only for confirmation with a patient's skin contours, but also to accommodate relative movement of the patient's skin.

It is well known that inadequate flexing and shaping of the electrode to a patient's contour can result in an irritation of the patient's skin. Electrical "hot spots" due to uneven electrode-skin contact can result in a rash or a burning sensation. A sensation of burning may be felt by a patient within a few minutes after application of the electrical signals during nerve and/or muscle stimulation, while rash conditions generally take a longer period of time to develop.

In order to provide uniform electrical coupling, heretofore developed electrodes have utilized conductive fabrics and foils in combination with a conductive adhesive in order to uniformly couple electrical signals to and/or from an electrical lead wire, or connector. A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, as well as U.S. Pat. No. 7,324,847, U.S. Pat. No. 5,904,712 CURRENT CONTROLLING ELECTRODE to Axelgaard. U.S. Pat. No. 4,736,752 teaches the control of current density across an electrode through the use of conductive ink design areas. These patents are incorporated in their entirety herewith by this specific reference thereto.

Many prior art electrodes have compromised the flexibility of the electrode in order to provide adequate current densities over the entire contact area of the electrode. Such electrodes typically have utilized a metallic mesh, or foil, to provide conductivity and utilize a conductive gel between the electrode and the patient's skin in order to accommodate the movement therebetween. Such use of foil or mesh often cause burning or hot spots at electrode edges.

The present invention is directed to a medical electrode having a pattern of island electrodes interconnected in a manner enabling adaptation to various body parts by energizing selective numbers of island electrodes in a desired pattern for each of the various body parts.

SUMMARY OF THE INVENTION

A medical electrode in accordance with the present invention generally includes a conductive member having a top and a bottom side and a plurality of cutouts establishing a pattern of islands interconnected by conductive member bridges.

A plurality of island electrodes are disposed on either the top or bottom side of the conductive member and on a corresponding island as hereinafter described in greater detail.

A conductive adhesive is disposed on the conductive member bottom side and covering the island electrodes disposed on the bottom side and also for adhering a medical electrode to a patient's skin. When the island electrodes are disposed on the top side of the conductive member adhesive it is present for adhering medical electrode to a patient's skin and transfer of electrical pulse thereto and therefrom.

Conductivity can be controlled in a number of manners. First, the conductive adhesive may be disposed on the conductive member only on the islands or alternatively can be disposed on the islands and the bridges. Further, the width of the bridges are narrower than the islands in order to provide electrode flexibility and also to control conductivity between the island electrodes.

Conductivity is further controlled when the conductive member is anisotropic having lower conductivity in a plane of the member compared to the transverse conductivity. Alternatively, the conductive adhesive may be an anisotropic having lower conductivity in a plane of the adhesive compared to transverse conductivity.

Various configurations of islands are contemplated, for example, the islands and island and electrodes may be rectilinear and the bridges interconnect the islands at sides thereof. Alternatively, the islands and island electrodes may be rectangular and the bridges interconnect the islands at corners thereof. Other geometric configurations are to be considered as included in the present application.

In addition, an indicia may be disposed on each bridge for indicating bridge severability options in order to provide a selected stimulation pattern to a patient.

A method of use of the electrode in accordance with the present invention includes selecting a body part for application of the electrode, severing selected bridges of the electrode corresponding to the selected body part, connecting at least one electrode contact point with an outside electronic device and applying the electrode to the body part.

BRIEF DESCRIPTION OF THE DRAWINGS

The present invention may be better understood with reference to the following detailed description taken in conjunction with the accompanying drawings in which:

FIG. 1 is a bottom plan view of an electrode in accordance with the present invention generally showing a conductive member with a plurality of cutouts establishing a honeycomb pattern of islands interconnected by conductive member bridges along with a plurality of island electrodes with each island disposed on the conductive member bottom side;

FIG. 2 is an exploded cross sectional view of the electrode shown in FIG. 1 additionally showing a conductive adhesive disposed on the conductive member bottom side;

DETAILED DESCRIPTION

Figure 3:
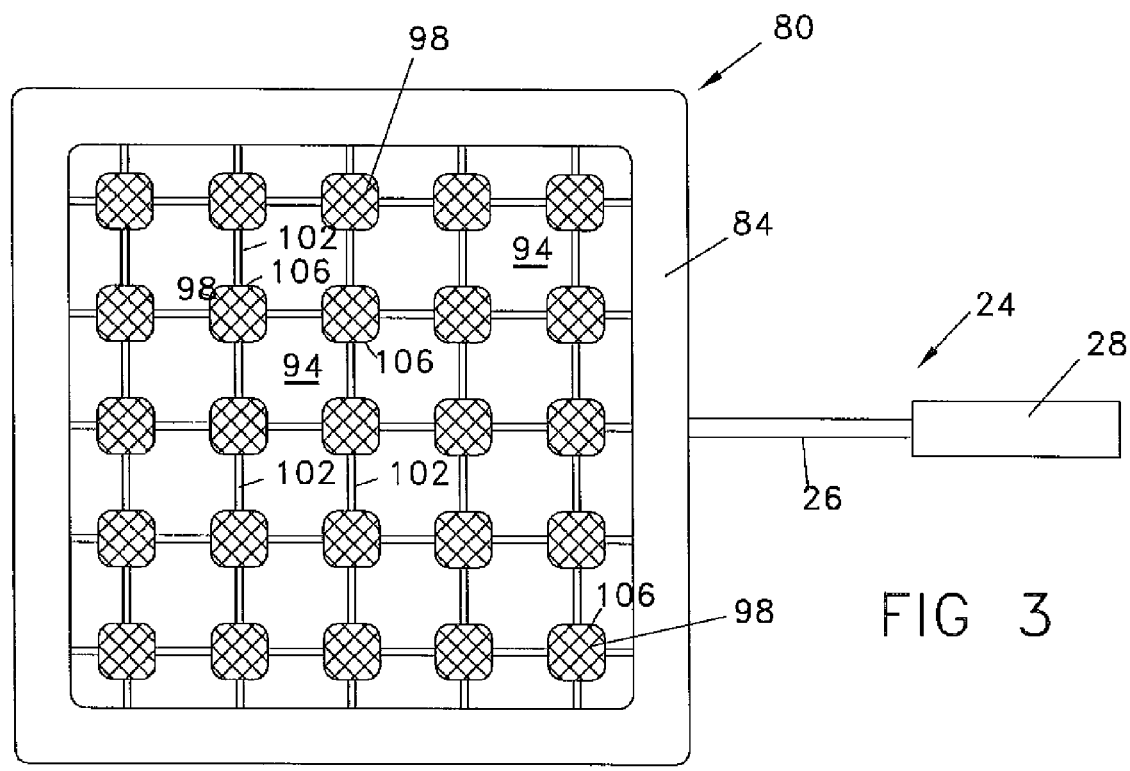
FIG. 3 is a plan bottom view of an alternative electrode in accordance with the present invention for generally showing a conductive member having a top and a bottom side and a plurality of cutouts establishing a honeycomb islands interconnected by conductive member bridges.

With regard to FIGS. 1 and 2, there is shown a medical electrode 10 in accordance with the present invention which generally includes a conductive member 14 having a top side 18 and a bottom side 20.

A connector 24 may be provided with a lead wire 26 and jack 28 for establishing electrical connection with the conductive member 14.

The conductive member 14 includes a plurality of cutouts 32 which effectively creates a pattern of islands 36 interconnected by conductive bridges 40.

Also shown in FIGS. 1 and 2 are a plurality of island electrodes 44 disposed on corresponding conductive member islands 36 on the conductive member bottom side 20.

The island electrodes 44 may be ink patterns as described in U.S. Pat. No. 7,324,847 hereinabove referenced and incorporated herewith which also describes the formulation of the conductive member 14 which may be formed from any suitable carbon loaded elastomeric film. Alternatively, the electrode 44 may be formed from any suitable metal, conductive coating or conductive plastic.

The bridges 40 are narrower than the islands 36 to provide electrode 10 flexibility in order to contour the electrode 10 to any body part (not shown).

With reference to FIG. 2, a conductive hydrogel adhesive 50 is disposed on the conductive member bottom side 20 which covers the island electrodes 44 and also adheres a medical electrode 10 to a patient's skin (not shown).

A plastic, paper, or other suitable carrier 54 along with a release coating 56 may be provided to prevent inadvertent and/or premature adhesion of the patient's skin or other object to the adhesive 50. The carrier 54 and release coating 56 are removed prior to application of the electrode 10 to the patient's body part (not shown).

Conductivity between the island electrodes 44 and a user's body part (not shown) may be controlled in a number of structural configurations. For example, the conductive adhesive 50 may be disposed only on the islands 36, or alternatively disposed on both the islands 36 and the bridges 40.

In addition, the conductive member 14 may be anisotropic having a lower conductivity in the plane of the member 14 compared to transverse conductivity. Alternatively, the conductive adhesive 50 may be anisotropic having a lower conductivity in the plane of the adhesive compared to transverse conductivity. Such flexible members and adhesives having anisotropic properties are available from 3M, St. Paul, Minn., see product data bulletin 73-73, "Grounded Heat Sink Bonding Film", September 2001, technical data sheet "Z-Axis Adhesive Film" March 2003 and technical Bulletin "Anisotropic Conductive Film Adhesive" January 2007. These references are to be incorporated herewith in their entirety for describing suitable films and adhesives for use in the present invention.

With further reference to FIG. 2, a cover sheet 58 and adhesive 60 may be provided to both insulate the conductive member 14 and attach the lead wire 26 to the conductive member 14.

An important feature of the present invention is the severability of the bridges 40 by a scissors, knife, or any suitable cutting device in order to create an active pattern of island electrodes 44 when provided with electrical impulses through non-severed bridges 40.

Various patterns of severability are indicated by indicia 62, see FIG. 1. Indicia 62 shown are not descriptive of any preferable severing of the bridges 40 but only illustrated as to the indication by way of ink or colored indicia to set forth the principal of the invention.

Figure 7:
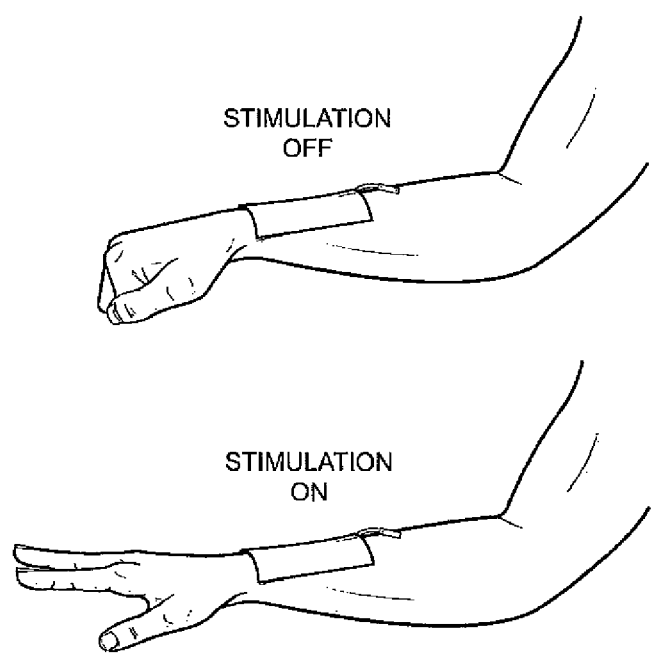
FIG. 7 is a perspective view of an electrode in accordance with the present invention attached to a forearm of a patient showing both the electrode in an off state and also in an activated state providing muscle stimulation.

The indicia 62 may include various patterns of different colors in order to sever the bridges 40 in a particular manner so that the electrode 10 may be applied to a specific body part, for example, an arm, an elbow, a wrist or a leg, a knee, an ankle with proper island electrode placement and activity for proper direction of electrical impulses into the selected body part (FIG. 7).

Accordingly, a method in accordance with the present invention using the electrode 10 includes selecting a body part (not shown) for application of the electrode 10 severing selected bridges 40 of the electrode corresponding to the selected body part, connecting at least one electrode contact point through the connector 24 to an outside electronic device and applying the electrode 10 to the selected body part.

The present invention is not limited to the geometric configuration shown in FIG. 1 which includes rectangular islands 36 and rectangular primary electrodes 44 interconnected by bridges 40 at corners 66 of the islands 36.

Figure 4:
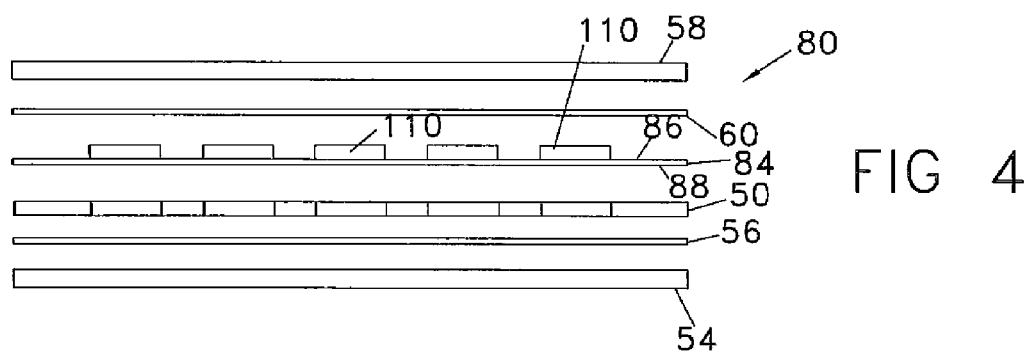
FIG. 4 is an exploded cross sectional view of the electrode shown in FIG. 3 also illustrating a plurality of island electrodes with each of the island electrodes being disposed on the conductive member top side.

An alternative example of an electrode 80 is shown in FIGS. 3 and 4 with common reference numbers indicating identical or substantially similar elements hereinabove described in connection with the electrode 10 shown in FIGS. 1 and 2. In this embodiment, a conductive member 84 having a top side 86 and bottom side 88 (see FIG. 4) with cutouts 94 establishing a honeycomb pattern of islands 98 with bridges 102 interconnecting the islands 98 at sides 106 thereof.

As shown in FIG. 4, in the electrode 80 island electrodes 110 are disposed on the top side 86 of the conductive member 84.

The remaining elements of the electrode 80 are indicated with reference characters common with those hereinabove described in connection with the electrode 10.

Figure 5:
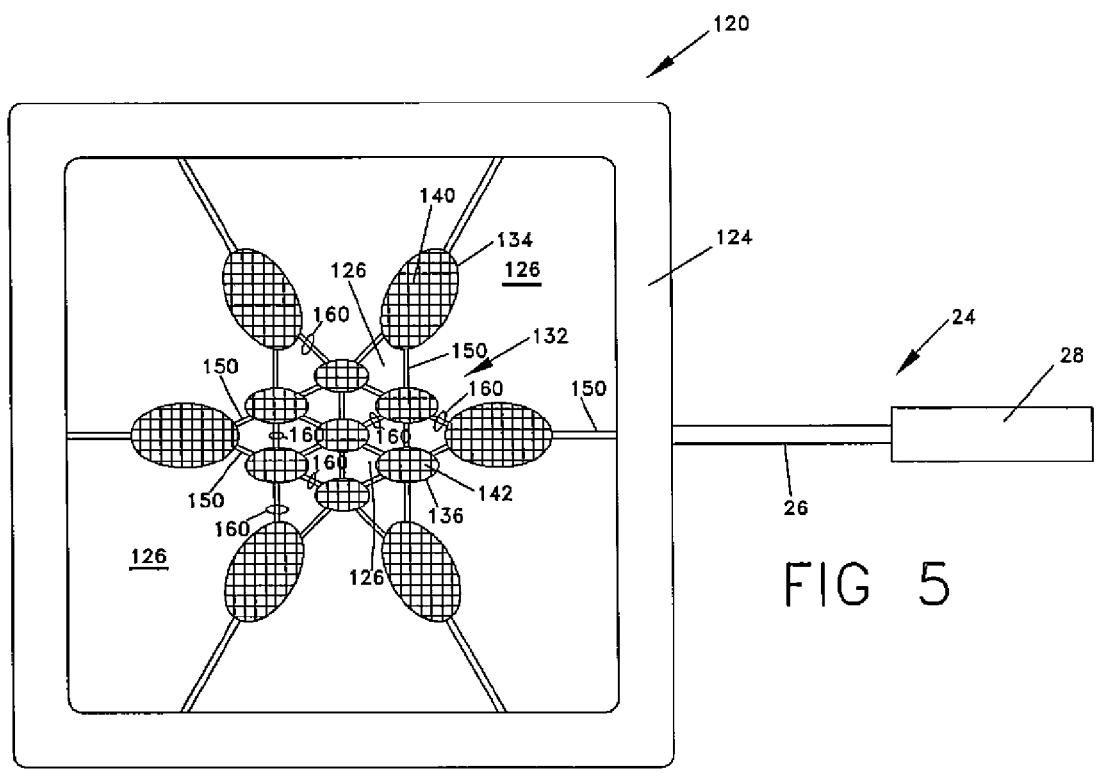
FIG. 5 is a plan bottom view of yet another embodiment of the present invention showing a clustered island arrangement for enabling confirmation with a selected body part.
Figure 6:
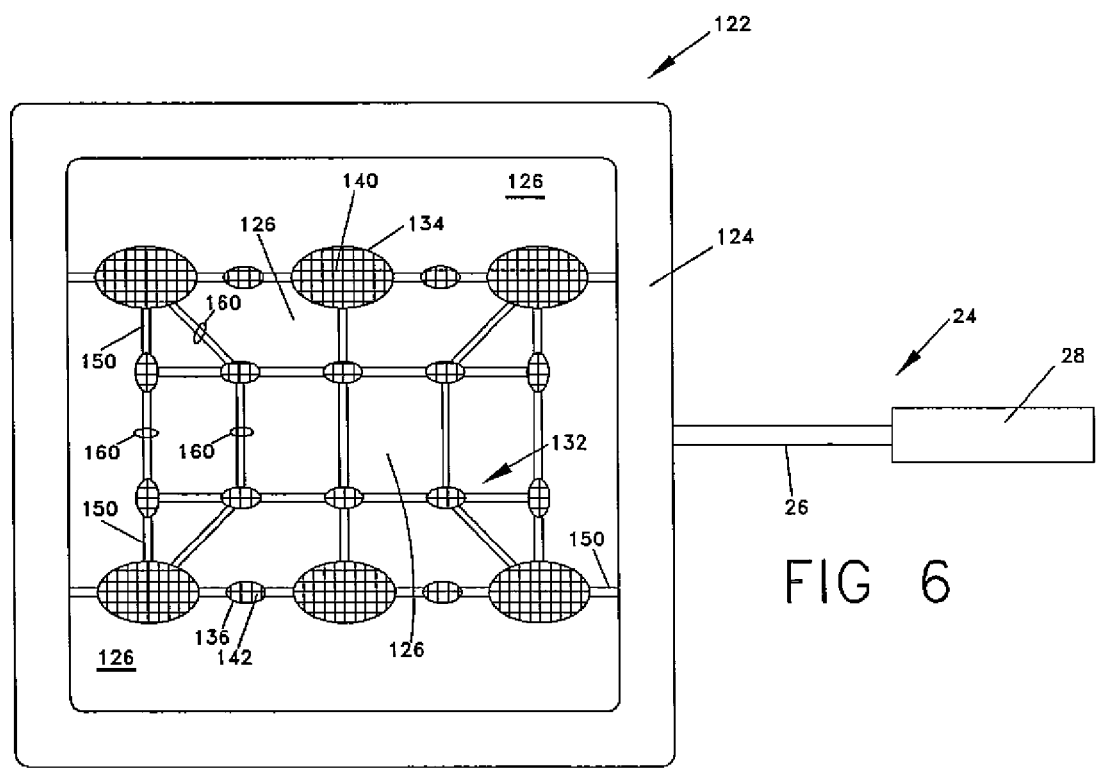
FIG. 6 is a plan bottom view of still another embodiment of the present invention illustrating an alternative clustered island array.

With reference to FIGS. 5 and 6, there are shown alternative electrode 120, 122 embodiments with the common reference characters relating to a equivalent or substantially similar elements of the electrode 10 shown in FIGS. 1 and 3. A conductive member 124 is provided with cutouts 126 to define a cluster 132 of islands 134, 136 which are arranged confirmation with a selected body part, not shown. Each of the islands 134, 136 include island electrodes 140, 142 as herein described in conjunction with the embodiments 10 and 80.

Bridges 150, similar to those hereinbefore described, interconnect the island electrodes 140, 142 to the conductive member 124. The size and shape of the islands 134, 136 and island electrodes 140, 142 are selected for providing a stimulation pattern into a selected body part, not shown, when deployed.

As hereinabove noted, indicia 160 disposed on each bridge 150 provide for indicating bridge 150 severability options in order to provide a selected pattern of active electrodes 140, 142 for providing stimulation to a body part, not shown. Only a limited number of indicia 160 are indicated in FIGS. 5 and 6 in order to provide a representation of this feature. All of the bridges 150 may be provided with indicia 160 which may be in the form of any color, numerical denotation, or mark enabling recognition of severability points for utilizing the medical electrode 120. In addition, the cluster 132 is provided only for illustration purposes and that many other clusters (not shown) may be utilized depending upon the ultimate positioning desired of the electrode 120 on a body part, not shown.

The size and shape of the islands 134, 136 and electrodes 140, 142 are also only representative with any number of size, shape, islands shape, island electrodes (not shown) considered to fall within the scope of the present invention.

FIG. 7 is a perspective view of an electrode attached to the forearm of a patient. In the upper view the electrode is in an off state and is not transmitting any electrical signals. The hand of the patient is shown in a closed state. The lower view shows the electrode in an activated state and accordingly the hand of the patient is open. The electrode can be configured to attach to the forearm or any other body part of the patient.

Although there has been hereinabove described a honeycomb or cluster type medical electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A medical electrode comprising:
   a conductive member comprising a top side, a bottom side and a plurality of cutouts, the plurality of cutouts establishing a plurality of conductive islands interconnected by a plurality of conductive member bridges;
   a single lead wire electrically coupled to the conductive member;
   a plurality of conductive island electrodes, each conductive island electrode disposed within a corresponding conductive island; and
   a conductive adhesive disposed on the conductive member bottom side for adhering the medical electrode to a patient's skin.

2. The medical electrode according to claim 1 wherein said conductive adhesive is disposed on the conductive member only on said islands.

3. The medical electrode according to claim 1 wherein said conductive adhesive is disposed on the conductive member on said islands and the bridges.

4. The medical electrode according to claim 1 wherein said plurality of island electrodes are selected from a group consisting of conductive ink, metal, conductive coating, and conductive plastic.

5. The medical electrode according to claim 1 wherein said bridges are narrower than the islands to provide electrode flexibility and control conductivity.

6. The medical electrode according to claim 1 wherein said conductive member is anisotropic having lower conductivity in a plane of the member compared to transverse conductivity.

7. The medical electrode according to claim 1 wherein said conductive adhesive is anisotropic having lower conductivity in a plane of the adhesive compared to transverse conductivity.

8. The medical electrode according to claim 1 wherein the island electrodes are disposed on the conductive member bottom side and are covered by the conductive adhesive.

9. The medical electrode according to claim 1 wherein the island electrode are disposed on the conductive member top side.

10. The medical electrode according to claim 1 wherein the islands and island electrode are clustered for conformation with a selected body part.

11. The medical electrode according to claim 1 wherein the islands and island electrodes are of different sizes.

12. The medical electrode according to claim 1 further comprising indicia indicating a bridge severability disposed on at least some of the plurality of conductive member bridges, wherein the indicia corresponds to at least two different stimulation patterns formed from the plurality of conductive island electrodes.

13. A medical electrode for delivering electric stimulation in selected stimulation patterns to a patient, said medical electrode comprising:
   a conductive member comprising a top side, a bottom side and a plurality of cutouts, the plurality of cutouts establishing a plurality pattern of conductive islands interconnected by a plurality of severable conductive member bridges;
   a single lead wire electrically coupled to the conductive member;
   a plurality of conductive island electrodes, each conductive island electrode disposed within a corresponding conductive island;
   a conductive adhesive disposed on the conductive member bottom side for adhering the medical electrode to a patient's skin; and
   indicia indicating a bridge severability disposed on at least some of the plurality of severable conductive member bridges, wherein the indicia corresponds to at least two different stimulation patterns formed from the plurality of conductive island electrodes.

14. The medical electrode according to claim 13 wherein said conductive adhesive is disposed on the conductive member only on said islands.

15. The medical electrode according to claim 13 wherein said conductive adhesive is disposed on the conductive member on said islands and the bridges.

16. The medical electrode according to claim 13 wherein said plurality of electrodes are selected from a group consisting of conductive ink, metal, conductive coating, and conductive plastic.

17. The medical electrode according to claim 13 wherein said bridges are narrower than the islands to provide electrode flexibility and control conductivity.

18. The medical electrode according to claim 13 wherein said conductive member is anisotropic having lower conductivity in a plane of the member compared to transverse conductivity.

19. The medical electrode according to claim 13 wherein said conductive adhesive is anisotropic having lower conductivity in a plane of the adhesive compared to transverse conductivity.

20. The medical electrode according to claim 13 wherein the island electrodes are disposed on the conductive member bottom side and are covered by the conductive adhesive.

21. The medical electrode according to claim 13 wherein the island electrode are disposed on the conductive member top side.

22. The medical electrode according to claim 13 wherein the islands and island electrode are clustered for conformation with a selected body part.

23. The medical electrode according to claim 13 wherein the islands and island electrode are of different sizes.

* * * * *